United States Patent [19]
Hui et al.

[11] Patent Number: 5,182,353
[45] Date of Patent: * Jan. 26, 1993

[54] METHOD FOR BONDING AN ANALYTE-SENSITIVE DYE COMPOUND TO AN ADDITION-CURE SILICONE

[75] Inventors: Henry K. Hui, Laguna Niguel; George A. Divers, III; Carmen Soikowski, both of San Diego, all of Calif.

[73] Assignee: Puritan-Bennett Corporation, Carlsbad, Calif.

[*] Notice: The portion of the term of this patent subsequent to May 14, 2008 has been disclaimed.

[21] Appl. No.: 557,624

[22] Filed: Jul. 24, 1990

Related U.S. Application Data

[63] Continuation-in-part of Ser. No. 394,637, Aug. 16, 1989, Pat. No. 5,015,715.

[51] Int. Cl.$^5$ .............................................. C08G 77/12
[52] U.S. Cl. ................................... 528/31; 528/15; 528/32; 528/10; 528/30; 528/43; 525/478
[58] Field of Search ............... 528/43, 15, 10, 31, 528/32, 30; 525/478

[56] References Cited

U.S. PATENT DOCUMENTS

| | | | |
|---|---|---|---|
| 3,904,373 | 2/1975 | Harper | 23/253 |
| 4,194,877 | 4/1980 | Peterson | 8/4 |
| 4,200,110 | 7/1980 | Peterson et al. | 128/634 |
| 4,468,229 | 3/1984 | Su | 8/507 |
| 4,568,518 | 11/1986 | Wolfbeis et al. | 422/56 |
| 4,657,736 | 3/1987 | Marsoner et al. | 422/56 |
| 4,712,865 | 11/1987 | Hsu et al. | 350/96.29 |
| 4,714,770 | 6/1987 | Hsu et al. | 556/419 |
| 4,746,751 | 5/1988 | Oviatt et al. | 556/456 |
| 4,906,249 | 2/1990 | Fogt et al. | 8/647 |
| 4,916,169 | 4/1990 | Boardman et al. | 522/27 |
| 4,921,589 | 2/1990 | Yates et al. | 204/157.5 |
| 4,925,268 | 5/1990 | Iyer et al. | 350/96.29 |
| 5,015,715 | 5/1991 | Divers et al. | 528/15 |

FOREIGN PATENT DOCUMENTS

| | | |
|---|---|---|
| 0283206A2 | 9/1988 | European Pat. Off. . |
| 0336986A1 | 10/1989 | European Pat. Off. . |
| 2132348A | 7/1984 | United Kingdom . |
| WO88/05533 | 7/1988 | World Int. Prop. O. . |

*Primary Examiner*—Melvyn I. Marquis
*Attorney, Agent, or Firm*—Fulwider Patton Lee & Utecht

[57] ABSTRACT

A method for covalently bonding an analyte sensitive dye compound to an addition-cure silicone is disclosed. The method includes a first step of functionalizing the dye compound to provide a linker arm with an isolated multiple bond. A second step include hydrosilylating the functionalized dye with polymethylhydrosiloxane. The resulting compound is cross-linked with vinyl-terminated polysiloxane in a third and final step.

2 Claims, No Drawings

METHOD FOR BONDING AN ANALYTE-SENSITIVE DYE COMPOUND TO AN ADDITION-CURE SILICONE

BACKGROUND OF THE INVENTION

1. Related Applications

This is a continuation-in-part of Ser. No. 07/394,637, filed Aug. 16, 1989, now U.S. Pat. No. 5,015,715.

2. Field of the Invention

The present invention is generally related to the measurement of concentrations of analytes in a fluid or gaseous mixture, and more specifically, to a method for making an improved oxygen-sensing optode in which the indicator substance is covalently bonded onto a matrix.

3. Description of Related Art

Fiber-optic based oxygen sensing apparatus have proliferated over the years due to their numerous applications in the medical, chemical and environmental fields. Many such oxygen sensors rely on the phenomenon of fluorescence quenching as a means for determining the presence of oxygen in a liquid or gaseous mixture and this approach has been quite attractive for such devices due to the high sensitivity that can be achieved. Systems and instruments implementing fluorescence quenching techniques utilize an encapsulated oxygen-quenchable fluorescence dye that is placed within a gas permeable matrix. The matrix is usually made from a polymer or similar substance. The dye/matrix element, generally referred to as a sensor element or optode, can be applied to the tip of an optical fiber using well-known techniques in the art. A light source with appropriate filtering system provides a select wavelength or wavelengths of light which is propagated down the optical fiber and excites the dye. The fluorescence signal, induced by the excitation energy, travels back through the same optical fiber and is collected by a photodetector near the proximal end of the fiber. Using techniques known in the art, the intensity of the fluorescence of the dye, which is a function of the oxygen level in the sample, can be transduced into a partial pressure of oxygen.

While many sensor elements or optodes have been developed for use with oxygen measuring devices, there are inherent problems associated with them that are detrimental to the accuracy of the measurements. For example, it is sometimes a difficult task to immobilize the fluorescent dye in a gas permeable matrix because of the chemical incompatibility between the dye and matrix. Many of the more widely used oxygen fluorescent dyes are polynuclear aromatic compounds which, because of their high degree of symmetry, usually have low solubility in organic materials. As a result, the fluorescent dyes have a tendency to leach through the permeable matrix into the solution or gas mixture that is being tested.

Various approaches for creating an operable sensor element include adsorbing the dye on inorganic or organic solid supports, dispersing the dye in the matrix by way of organic solvents, and covalently bonding the dye on porous glass. While useful under some circumstances, many of these techniques still have serious drawbacks if the dye is chemically incompatible with the polymer matrix. Furthermore, these dyes still have a tendency to leach out, particularly when in contact with a sample that includes a substance that has similar properties to the dye/polymer matrix being used for the optrode. Unfortunately, such substances include blood proteins and many organic solvents, which are often the samples being tested. As a result of the leaching of the dye during use, the sensing element may have to be routinely replaced to ensure the accuracy of oxygen measurements. Moreover, symmetrical dye molecules that are free to move within a polymer matrix tend to agglomerate which results in changes in fluorescent properties.

Accordingly, those concerned with the development and use of oxygen sensing devices have long recognized the need for an improved method for creating a sensor element that will not leach when placed in the sample solution or during storage and will not suffer dye agglomeration over time. Preferably, the improved method should produce a dye/matrix that can be readily affixed to the end of an optical fiber or other similar device in a single step. Moreover, the sensor made according to the method should be relatively inexpensive to manufacture and should provide accurate oxygen measurements. It would also be advantageous if the method were able to provide relatively high yields of quality sensors.

SUMMARY OF THE INVENTION

The manufacture of economic quantities of fluorescent sensors to be used in combination with optical fiber systems to measure blood oxygen levels has become very important as the use of such sensors has increased. In particular, methods to manufacture sensors which resist leaching, are stable over time and result in high yields from a given quantity of materials are very advantageous. The present invention provides these benefits in a new and novel process which results in economically advantageous yields of sensors which are resistant to leaching of the dye from the matrix.

The present invention provides a method of manufacture for which a sensor element in which a polynuclear aromatic dye compound is covalently bonded to an addition-cure silicone to thus provide a sensor for the detection of oxygen in fluids that is sensitive, resists leaching and other degradation and can be produced in a relatively simple process with high yields. The method of the invention is a three-part process which first requires that the polynuclear aromatic dye be functionalized to provide a linker arm with isolated multiple bonds to lower the degree of symmetry of the dye and thereby increase its solubility when placed in a polymer matrix. The next step of the method includes the hydrosilylation of the functionalized dye with polymethylhydrosiloxane to form a compound that can be later cross-linked with vinyl-terminated polysiloxane in a final step.

The dye, when contained in the polysiloxane according to the present invention exhibits high sensitivity of the fluorescent quenching function in the presence of oxygen, which makes it extremely advantageous for use in optical systems that measure concentrations of oxygen gas. The dye/matrix structure results in the formation of a cross-linked silicone rubber with the dye covalently bonded to it. The cross-linked silicone can be made to assume various advantageous characteristics by substitutions on the vinyl-terminated polysiloxanes. Viscosity and physical strength of the silicone can also be varied by changing the molecular weight of the polysiloxane. As a result, the dye of the sensor of the present invention is less susceptible to leaching or agglomeration. A sensor element made in accordance with the method of the present invention can be more accurate than prior art sensors.

Other features and advantages of the present invention will become apparent from the following detailed description, taken in conjunction with the accompanying diagrams and equations, which illustrate, by way of example, the principles of the invention.

DETAILED DESCRIPTION OF THE INVENTION

Oxygen sensors which utilize fluorescent dyes, the output of which is quenched in proportion to the concentration of oxygen in a sample to be evaluated are well known in the art.

The present invention is embodied in a new and novel method for bonding an oxygen-sensitive indicator substance to an addition-cure silicone to form a sensor element that is particularly resistant to leaching of the indicator substance through the polymer matrix. The oxygen-sensitive fluorescent indicator substance is typically a polynuclear aromatic compound. The matrix may be an addition-cure silicone which provides a gas-permeable substance that is hydrophobic and prevents leaching of the indicator dye out of the matrix, since the dye is bonded to the silicone.

The method of the present invention by which the polynuclear aromatic compound is bonded to the addition-cure compound can be divided into the following three basic processes:

First, a dye indicator is functionalized to provide a linker arm with an isolated multiple bond.

Second, the functionalized dye indicator is hydrosilylated with polymethylhydrosiloxane to form an intermediate compound.

Lastly, this intermediate compound is cross-linked with vinyl-terminated polysiloxane to form the dye/matrix.

The polynuclear aromatic dye compound used for sensors has a high degree of symmetry that results in its low solubility in organic materials. As a result, it has been found to be advantageous to first functionalize the dye to lower its degree of symmetry, thereby increasing its solubility in the polymer matrix. The functionalization step provides a linker arm with a terminal multiple bond. This linker arm helps minimize steric interaction between the dye and the polymer. Moreover, the linker arm provides a means to locate the multiple bond remote from the conjugated aromatic systems. In practice, it has been found that the length of the linker arm may be from $n=0$ to $n=500$ and may advantageously have a length of $n=1$ to 22.

The linker arm essentially may consist of a hydrocarbon chain or it may contain heteroatoms such as oxygen, nitrogen, sulfur, phosphorus, or silicone. The isolated multiple bond can be any one from a group that includes a carbon-carbon, a carbon-oxygen, a carbon-nitrogen or a nitrogen-nitrogen bond. Any chemical method which results in the addition of a linker arm and an isolated multiple bond to the dye molecule is contemplated by the present invention and falls within the spirit and scope of the invention.

The polynuclear dye compounds which may be used with the method of the present invention include, but are not limited to, perylene, benzoperylene, coronene, decacyclene and others that are functionally similar. The chain length of the linker arm can range from $n=1$ to 22. The multiple bonds can be a double or triple bond.

The following examples are included for further understanding of the invention. The first two examples show two methods for completing the functionalization step. It should be understood that these examples are included for the purpose of illustration but are not intended to limit the scope of the present invention.

A FIRST PREFERRED EMBODIMENT DEMONSTRATING THE FUNCTIONALIZATION STEP

In a first preferred embodiment of the first step of the method of the present invention, a polynuclear aromatic compound, namely benzoperylene, is formylated with α, α-dichloromethyl methyl ether in a Friedal-Crafts acylation reaction. The yield from this mixture was 1-benzoperylene carboxaldehyde as illustrated in the following equation:

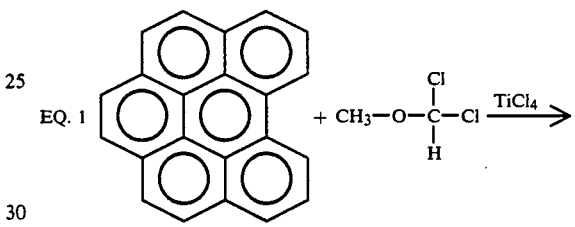

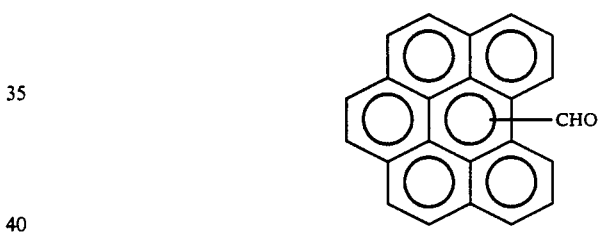

The 1-benzoperylene carboxaldehyde was reduced with LiAlH$_4$ which results in the formation of 1-benzoperylene methyl alcohol. Equation 2 describes this reaction and is shown below:

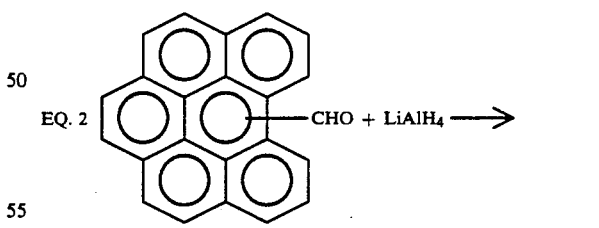

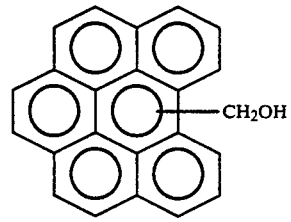

This method alcohol is treated with 8-bromo-1-octene in DMSO/NaOH to from 8-octenyl benzoperylene methyl ether. Equation 3 which describes this reaction appears below:

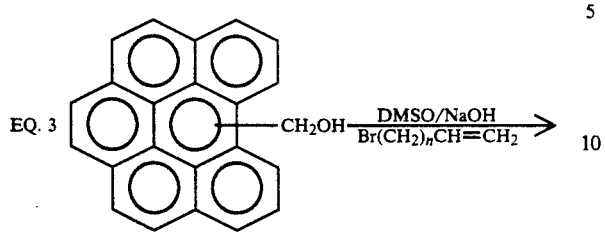

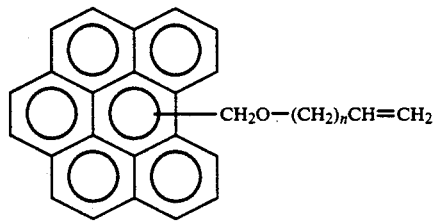

Analogous reactions with 3-bromo-1-propene, 4-bromo-1-butene and 6-bromo-1-hexene, shown in Equation 3 above, provide corresponding ethers.

A SECOND PREFERRED EMBODIMENT DEMONSTRATING THE FUNCTIONALIZATION STEP

In a second preferred embodiment of the functionalization step of the present invention, benzoperylene is again chosen as the polynuclear aromatic compound. Butyllithium/TMEDA (tetramethylethylenediamine) was added to the benzoperylene in tetrahydrofuran at room temperature to generate benzoperylene carbanion. This carbanion is quenched with 3-bromo-1-propene, 4-bromo-1-butene, 6-bromo-1-hexene and 8-bromo-1-octene resulting in the formation of substituted benzoperylene with different hydrocarbon chain lengths. Equation 4 below describes this reaction:

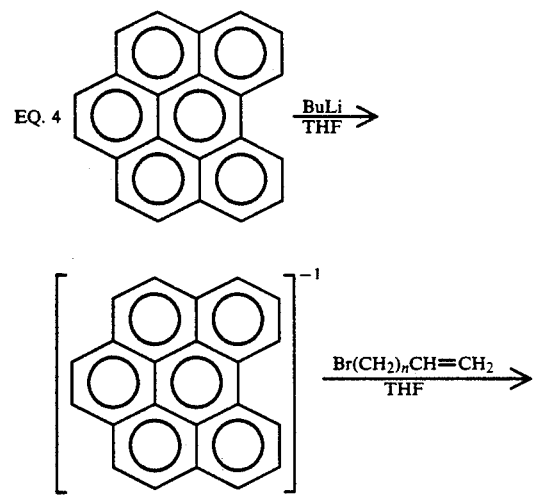

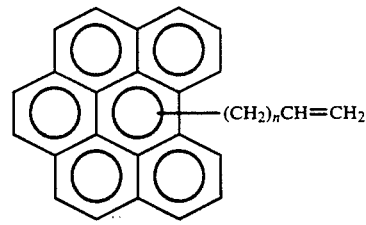

where n = 1, 2, 4, 6

A THIRD PREFERRED EMBODIMENT DEMONSTRATING THE FUNCTIONALIZATION STEP

In a third preferred embodiment the first step of the present invention, coronene is used as the polynuclear aromatic compound. In a dry, 1.0 liter round bottom flask, 1.0 g of coronene (3.3 mmol) is dissolved in an 80/20 solution of THF/HMPA (hexamethylphosphonamide). The solution is then cooled to $-50°$ C. over a period of 15 minutes. To this solution is added 5.0 ml of TMEDA (33.1 mmol) and 16.5 ml of n-Butyllithium (33.1 mmol). The dark blue solution is stirred at $-50°$ C. for 30 minutes. After 15 minutes of stirring, 1.20 ml of 8-bromo-1-octene (10.0 mmol) is added to the mixture. The temperature is then maintained at $-45$ to $-55°$ C. for three hours. The reaction mixture is then allowed to warm up to room temperature overnight. Isopropyl alcohol (100 ml) is added to quench the remaining n-BuLi. The reaction mixture is then rotary evaporated to remove the THF. The resulting brown residue is dissolved in toluene in and washed seven times with deionized water ($7 \times 200$ ml) to remove the HMPA. The remaining organic layer is separated, dried over MgSO$_4$, and rotary evaporated to dryness. The resulting brown liquid is purified on an DNAA silica gel column with a mobile phase of 90/10 hexane/CH$_2$Cl$_2$. The product fractions are then collected and rotary evaporated to dryness. A silica gel prep plate is run, with 90/10 hexane/CH$_2$Cl$_2$ as the mobile phase, to remove any impurities. The product band was excised from the prep plate and washed with 200 ml of CH$_2$Cl$_2$. The CH$_2$Cl$_2$ was rotary evaporated to yield 700 mg of the fluorescent green product.

NMR data (CDCl$_3$): 3.31 (dd, 2H, Ar—CH$_2$)
4.92 (dd, 2H, =CH$_2$)
5.76 (m, 1H, —CH=)
7.81–8.91 (m, 11H, aromatic protons)

An important benefit derived from the use of a cosolvent of THF and HMPA in this preferred embodiment of the first step of the method is the improved yield of the process over those embodiments utilizing THF only. It has been found that this process provides a yield 35 times greater than the process utilizing THF only (e.g. 70% yield compared to 2%), thereby dramatically and unexpectedly improving the economy and efficiency of the process. This fact, when combined with the other benefits of the method, results in important advantages from the use of the invention in the manufacture of fluorescent intravascular sensors.

Equation 5 below describes the reaction:

EQ. 5

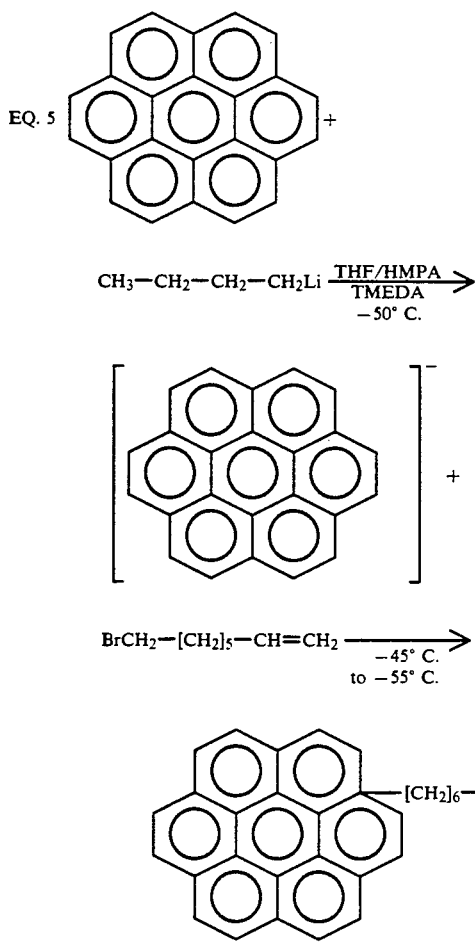

$CH_3-CH_2-CH_2-CH_2Li \xrightarrow[-50°C.]{THF/HMPA \atop TMEDA}$ $BrCH_2-[CH_2]_5-CH=CH_2 \xrightarrow[to -55°C.]{-45°C.}$

THE SECOND STEP OF THE METHOD OF THE INVENTION

The second step of the method, the hydrosilylation of the functionalized polynuclear aromatic compound with polymethylhydrosiloxane, can be performed by several well known methods. The following formula discloses a typical polymethylhydrosiloxane:

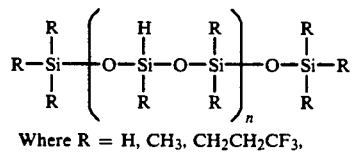

Where R = H, $CH_3$, $CH_2CH_2CF_3$, $CH_2(CH_2)_nCH_3$ and phenyl

Polymethylhydrosiloxanes are available with different degrees of Si-H substitutions and different R group functionalities. The amount of Si-H substitutions will determine the number of dye molecules that can be bonded to the polymer. The type of R group on the polymethylhydrosiloxane will determine the refractive index of the polymer and the solubility of the dye molecule in the silicon reaction mixture. The higher the solubility of the dye in the polymer, the more likely the dye will bond.

A FIRST PREFERRED EMBODIMENT DEMONSTRATING THE HYDROSILYLATION STEP

In a first preferred embodiment of the hydrosilylation step of the present invention, a reaction mixture which consists of 15 mg of 8-octenyl coronene ($4 \times 10^{-2}$ mmol), 1 g of polymethylhydrosiloxane (50%-55%) SiH, 8 mmol) and 1 drop of 10% platinic acid was heated to 120° C. under an inert atmosphere for 16 hours (See EQ 6 below)—with the solid dye compound slowly solubilizing into the polymer. At the end of the reaction period, the dye-bound silicone liquid was filtered through Celite to remove impurities.

EQ. 6

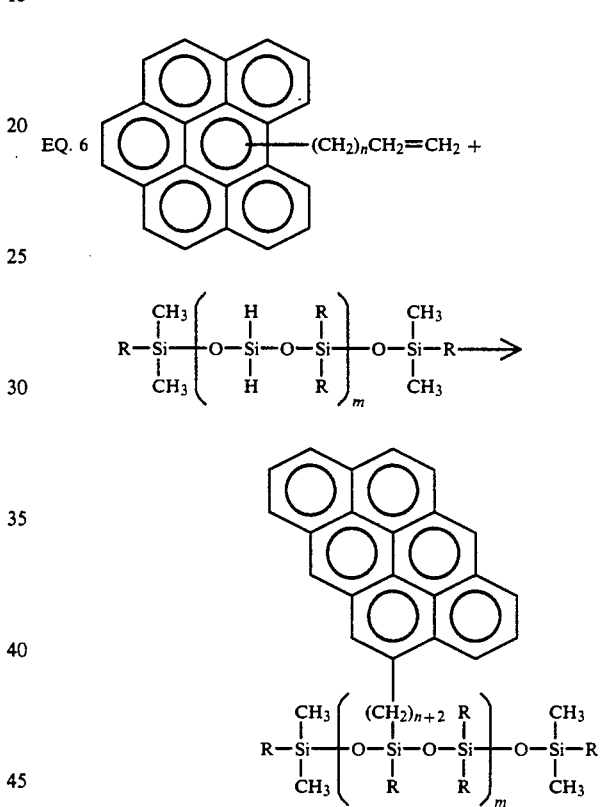

This scheme provides flexibility to vary the dye concentration by changing the percent Si-H substitution on the polymethylhydrosiloxane. The refractive index and physical strength of the polymer can be changed by varying R. The dye/polymer is extremely stable when stored in a dark and cool environment.

A SECOND PREFERRED EMBODIMENT DEMONSTRATING THE HYDROSILYLATION STEP

In a second preferred embodiment of the hydrosilylation step, a reaction mixture which consists of 5-100 mg of 8-octenyl coronene, 1.0 g of polymethylhydrosiloxane (50%-55% Si-H), 200 mg of cyclohexane (20% of the polymethylhydrosiloxane) and 1-20 drops of 20% platinum/vinylsiloxane catalytic complex in cyclohexane, was heated to 80°-130° C. for 2-15 hours under an inert atmosphere. At the end of the reaction period, the cyclohexane was removed by purging with $N_2$ and the resulting mixture was filtered through a celite/glass wool plug to remove impurities.

THE THIRD AND FINAL STEP OF THE METHOD OF THE INVENTION

The final step of the method, the cross-linking of the polysiloxane with the hydrosilylated polynuclear aromatic compound, can also be accomplished using known techniques in the art. For example, a mixture of dye/polyhydrosiloxane and vinyl-terminated polysiloxane when heated in the presence of platinum catalyst, results in the formation of a cross-linked silicone rubber with dye covalently bonded to it. The cross-linked silicone can take on different characteristics by changing substitutions on the vinyl-terminated polysiloxanes. Viscosity and physical strength of the silicone can also be varied by changing the molecular weight of the polysiloxane.

A FIRST PREFERRED EMBODIMENT ILLUSTRATING THE CROSS-LINKING STEP

In a first preferred embodiment of the final step of the process, 10 mg of dye/polyhydrosiloxane and 50 mg of vinyl-terminated polymethylphenylsiloxane with 5 ppm of platinum catalyst is mixed in an aluminum dish. The silicone mixture is degassed under a vacuum and was applied to the optical fiber. The chemistry is then cured by heating the fiber tip in an oven at 100° C. for 1 hour.

A SECOND PREFERRED EMBODIMENT ILLUSTRATING THE CROSS-LINKING STEP

In a second preferred embodiment of the final step of the process, 10 mg of dye/polyhydrosiloxane is mixed with 90 mg of hexane. To this mixture is added 80 mg of vinyl-terminated polymethylphenylsiloxane. The mixture is then stirred and promptly applied to the optical fiber. The chemistry is cured by heating the fiber tip in an oven at 100° C. for 1 hour.

In order to evaluate the performance of a sensor formed according to the method of the invention, our optical fiber including a quantity of the cured matrix at its distal end was connected to an instrument which provides means to activate and read the output of the sensor. The fiber tip was placed in a saline solution and 7% $O_2$ gas was introduced. When the chemistry was irradiated with 380 nm light, the emission at 440 nm yielded a normalized voltage of 2.857 V. When the concentration of $O_2$ was increased to 20%, the resulting voltage was 1.934 V. A voltage of 2.852 V was registered when the $O_2$ level was reverted back to 7% showing reversibility and no hysteresis. The sensing tip was also placed in media such as methylene chloride, methyl alcohol, isopropyl alcohol, silicone liquids, and bovine blood. No noticeable drop in signal was observed.

From the above examples, it is evident that the present invention provides a chemical method for covalently bonding a polynuclear aromatic dye to an addition-cure silicone. While several particular forms of a method in accordance with the present invention have been described, it will also become apparent to those skilled in the art that various modifications may be made without departing from the spirit and scope of the invention. Accordingly, it is not intended that the invention be limited, except as by the appended claims.

We claim:

1. A method for bonding an analyte-sensitive indicator substance selected from the group consisting of perylene, benzoperylene, coronene, and decacyclene to addition-cure silicone to form a sensor element, comprising the steps of:
    adding butyllithium and tetramethylethylenediamine to the indicator substance in a tetrahydrofuran/hexamethylphosphoramide solvent system to generate a mixture containing the carbanion of the indicator substance;
    adding 8-bromo-1-octene to the indicator substance carbanion mixture to form a functionalized indicator substance;
    reacting the functionalized indicator substance with polymethylhydrosiloxane to form an indicator-bound silicone liquid; and
    cross-linking the indicator-bound silicone liquid with vinyl-terminated polysiloxane to form said sensor element.

2. The method of claim 1, wherein the indicator substance is coronene.

* * * * *